United States Patent [19]
Abe et al.

[11] Patent Number: 4,778,816
[45] Date of Patent: Oct. 18, 1988

[54] ANTI-ASTHMATIC COMPOSITION AND PROCESS FOR PREPARING THE SAME

[75] Inventors: Tooru Abe, Sagamihara; Yukiyoshi Yanagihara, Machida; Takao Shida, Sagamihara; Shigekatsu Kohno, Ohtsu; Katsuya Ohata, Uji; Yoshiaki Ogasawara, Odawara; Shinji Kageyama, Kanagawa; Touru Oguma; Yoshihiro Tsuriya, both of Hatano; Toshio Kuroda, Sagamihara; Terumasa Hashimoto, Kawasaki, all of Japan

[73] Assignee: Wakamoto Pharmaceutical Co., Ltd., Tokyo, Japan

[21] Appl. No.: 776,771

[22] Filed: Sep. 17, 1985

[30] Foreign Application Priority Data

Dec. 24, 1984 [JP] Japan ................................ 59-270939
Mar. 29, 1985 [JP] Japan ................................ 60-63320

[51] Int. Cl.⁴ ........................................... A61K 31/41
[52] U.S. Cl. ..................................... 514/381; 514/826; 548/253
[58] Field of Search ................................ 514/381, 826

[56] References Cited

U.S. PATENT DOCUMENTS 4,400,381 8/1983 Favier et al. .................. 424/248.52
4,432,986 2/1984 Frickson et al. ................ 514/826 X
4,442,115 4/1984 Ramspen et al. ................ 514/826 X
4,443,460 4/1984 Rodriquez et al. ............. 514/826 X

FOREIGN PATENT DOCUMENTS 0040673 4/1981 Japan .
57-11975 1/1982 Japan .

OTHER PUBLICATIONS

Chemical Abstracts 96: 217856 a (1982).
Agata et al., Japan. J. Pharmacol. 32:689–697 (1982).
May et al., J. Allerg., vol. 46, No. 1, pp. 12–20 (1970).

Primary Examiner—Leonard Schenkman
Attorney, Agent, or Firm—Burns, Doane, Swecker & Mathis

[57] ABSTRACT 5-(3-n-Butyloxalylaminophenyl) tetrazole having an excellent SRS-A release-inhibiting effect is used as an effective component for an anti-asthmatic agent, and a pharmaceutical preparation obtained by mixing the tetrazole with a specific dispersant such as polysorbate-80 in coexistence with a non-aqueous solvent shows high dissolubility and bioavailability.

10 Claims, No Drawings

ANTI-ASTHMATIC COMPOSITION AND PROCESS FOR PREPARING THE SAME

BACKGROUND OF THE INVENTION

1. Field of the Invention

This invention relates to an anti-asthmatic agent, a method for the treatment of asthma, a pharmaceutical composition for the treatment of asthma and a process for preparing the pharmaceutical composition.

2. Description of the Prior Art

Asthma is a disease marked by paroxysmal dyspnea and stridor, which is caused by airway stenosis.

Typical causes of airway stenosis are constriction of airway smooth muscle, formation of edema in airway mucous membrane, exasperation of airway discharge and formation of mucocele in airway, among which the most important is the constriction of airway smooth muscle.

An asthma patient generally has an elethitic airway, which is liable to produce IgE antibody against many antigens including inhaled allergen. Therefore, asthma patients carry a large quantity of IgE antibody in their bodies, and if they inhale antigens such as pollen and the other allergens, and antigen-antibody reaction is liable to take place at the surface of mast cell existing abundantly in airway submucosa, and the release of histamine and SRS-A, (slow reacting substance of anaphylaxis), is triggered by the reaction, which causes asthma symptoms including the constriction of the smooth muscle (Progress in Medicing, Vol. 3, pages 655-666, 1983 published by Life Science K.K. Japan).

The spasm of bronchial smooth muscle by histamine is very sensitive, evanescent and strong, and serious paroxysm is over within a comparatively short time (Allergy, Vol. 7 pages 93-104, 1958.

In contrast, the constriction of bronchial smooth muscle by SRS-A occurs slowly, but continuously and strongly for a long period of time, which causes serious pain to the asthma patient. Therefore, the development of a medicine which can effectively inhibit the release of SRS-A has been desired (Progress in Medicine, Vol. 3, pages 655-666, 1983).

SRS-A is released from mast cells, or the like, by an antigen-antibody reaction in which an IgE antibody participates. Unlike histamine belonging to a preformed mediator, SRS-A is synthesized by the stimulation of the reaction and belongs to a newly generated mediator essentially consisting of leucotrienes $C_4$, $D_4$, $E_4$ ($LTC_4$, $LTD_4$, $LTE_4$) which are formed by a series of reactions, including the reaction of arachidonic acid initiated by 5-lipoxygenase, and whose chemical structures have been clarified (Meneki Yakuri, Immunology and Pharmacology), Vol 2, No. 2, pages 207-213, 1984).

As disclosed in Japanese Patent Public Disclosure No. 11975/1982, 5-(3-n-butyloxalyl-aminophenyl) tetrazole (MTB) is a compound which was synthesized in the Research Division of the Company in which the applicants are employed and was found to show an anti-allergic action. The compound has the following chemical formula.

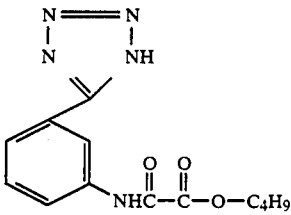

Although it is known that MTB has an anti-allergic action, inhibiting the release of histamine, it has not been known that MTB has excellent SRS-A release-inhibiting action (Japanese Journal of Pharmacology, Vol. 32, pages 689-697, 1982).

SUMMARY OF THE INVENTION

An object of the present invention is to provide a novel anti-asthmatic agent.

Another object of the present invention is to provide a novel method for the treatment of asthma.

Still another object of the present invention is to provide a novel pharmaceutical composition for the treatment of asthma.

A further object of the present invention is to provide a novel process for preparing the pharmaceutical composition.

Other and different objects, advantages and features of the present invention will become apparent to those skilled in the art upon consideration of the following detailed description and claims.

Aiming at the development of an anti-asthmatic agent, the inventors of this invention noticed that the substance playing the most important role in aggravating asthma symptoms is SRS-A and conducted extensive screening tests to find a compound which can effectively inhibit the release of SRS-A. As a result, they have found that MTB is a compound which meets the purpose.

Next, they conducted research to improve the pharmaceutical preparation of MTB as a medicine and found that since an original powder of MTB is practically insoluble in water, it is very unmanageable during the pharmaceutical preparation. Further they found that when the original powder as such is pharmaceutically prepared in a conventional manner, the pharmaceutical preparations obtained are inferior as regards disintegration and dissolution properties, resulting in insufficient bioavailability of the effective component. As a result of extensive studies to solve these problems, they have completed the present invention relating to an anti-asthmatic agent and a process for pharmaceutically preparing the same.

DETAILED DESCRIPTION OF THE INVENTION

The present invention relates to an anti-asthmatic agent (hereinafter referred to as the present medicine) comprising, as an effective component, MTB in an amount showing an SRS-A release-inhibiting effect, a method for the treatment of asthma, a pharmaceutical composition (hereinafter referred to as the present composition) for the treatment of asthma and a process for preparing the pharmaceutical composition.

The present invention provides an anti-asthmatic agent which comprises, as an effective component, 5-(3-n-butyloxalyl-aminophenyl) tetrazole (hereinafter referred to as MTB) in an amount showing an SRS-A release-inhibiting effect. MTB has an excellent SRS-A release-inhibiting action and histamine release-inhibiting action. When administered to an asthma patient, MTB effectively inhibits the release of the above mentioned two components which cause asthma, and shows excellent effects as an anti-asthmatic agent.

The present composition is usually used as an orally administered preparation in a form such as tablet, granule, powder, capsule or the like, but can also be used as an inhalant, suppository, cataplasm, injection or the like.

The present medicine shows excellent anti-asthmatic effect and a normal unit dose is about 10 to about 500 mg, preferably about 50 to about 300 mg for an adult.

In preparing the present composition, the conventional procedures may be employed. However in order to increase the bioavailability, it is preferable to employ a new process which comprises: (i) uniformly mixing MTB and at least one component selected from the group consisting of polysorbate-80, polyvinyl pyrrolidone (hereinafter referred to as PVP), polyoxyethylene hardened castor oil, polyethylene glycol (hereinafter referred to as PEG), hydroxymethyl cellulose, hydroxypropyl cellulose and hydroxypropyl methyl cellulose (the selected components being hereinafter referred to as the specific dispersant) in coexistence with a non-aqueous solvent and thereafter removing the non-aqueous solvent from the mixture or (ii) dissolving MTB into a liquid PEG to cause MTB to be included into the liquid PEG. If necessary, it may be diluted with a pharmaceutically acceptable carrier. The inert solvent utilized in this process (hereinafter referred to as the new preparation process) may be of any type insofar as it dissolves or disperses both MTB and the specific dispersant simultaneously, and is easily evaporated off. However there are usually used such solvents as methanol, ethanol, isopropanol, acetone and dichloromethane. They are used alone or in combination.

The specific dispersant is composed of a relatively high molecular component which is dissolved or dispersed in both water and a non-aqueous solvent. Although the amount of the specific dispersant used varies considerably depending on the kind thereof, it is usually selected in the range of 0.01 to 10 parts by weight per one part by weight of MTB.

PEG having an average molecular weight of about 200 to about 6,000 is preferably used.

The inert carrier may be any type insofar as it is pharmaceutically acceptable. Usually crystalline cellulose, corn starch, mannitol, light silicic acid anhydride, kaoline and the like can be used.

According to the new preparation process, the effective component MTB is dissolved or dispersed in a non-aqueous solvent together with the specific dispersant, followed by the evaporation of the solvent to form a solid solution or a co-precipitate, whereby a pharmaceutical preparation is obtained. Alternatively, if PEG is liquid, there is provided a pharmaceutical preparation where MTB is dissolved in the PEG. Therefore the present medicine prepared by the new preparation process has a high bioavailability due to its excellent dispersability and dissolubility.

Measurement by a differential thermal scanning calorimeter (DSC 30 type manufactured by Shimadzu Corporation, Japan) clarified that MTB shows a peak of absorption indicating the crystal structure, whereas the product obtained by mixing MTB with the specific dispersant in coexistence with the non-aqueous solvent does not show such a peak. From this observation, it has been confirmed that the treatment with the non-aqueous solvent in the new preparation process not only increases the mixing efficiency but also brings about a change in the crystal structure itself of MTB.

Alternatively, in the new preparation process, a premix containing a high concentration of MTB may be first prepared by using no carrier or a limited amount of carrier and the resulting premix may be diluted with a carrier in a conventional manner to obtain a pharmaceutical preparation of any form. In addition, a larger amount of the specific dispersant may be used, which also serves as a carrier.

Usually it is convenient to obtain a granule product, powder product or the like in a wet process wherein MTB is simultaneously mixed with a conventionally used carrier, binder, sweetener and other auxiliaries in coexistence with a non-aqueous solvent. If necessary, the granule product, powder product or the like is conveniently charged into a capsule to obtain a capsule product or tableted to obtain a tablet product.

Even when MTB and the specific dispersant are not completely dissolved in a non-aqueous solvent, the MTB preparation still shows an unexpectedly high dissolubility.

Hereunder the present invention will be further described referring to non-limitative examples.

EXAMPLE 1

To a mixture of 50 g of MTB, 44 g of crystalline cellulose, 10 g of corn starch and 10 g of hydroxypropyl cellulose with a low degree of substitution, there was added 6 g of PVP dissolved in 30 ml of isopropanol, and the resulting mixture was mixed uniformly, followed by granulating, drying at 40° C. for 5 hours and sieving to obtain a fine granule product.

EXAMPLE 2

A fine granule product was obtained in the same manner as in Example 1 except that 4 g of PVP and 2 g of polysorbate-80 were used in place of 6 g of PVP. The fine granule product obtained above was then charged into a hard gelatin capsule to obtain a capsule product.

EXAMPLE 3

To 100 g of MTB dissolved in 500 ml of acetone, there was added 10 g of polysorbate-80 to obtain a mixture. After the mixture was agitated, 400 g of crystalline cellulose, 50 g of hydroxypropyl cellulose with a low degree of substitution and 440 g of corn starch were added thereto, followed by uniform mixing, drying at 50° C. for 5 hours and sieving to obtain a powder product.

EXAMPLE 4

To a mixture of 100 g of MTB, 420 g of crystalline cellulose, 400 g of corn starch and 30 g of hydroxypropyl cellulose with a low degree of substitution was added 50 g of PVP dissolved in 550 ml of isopropanol, and the resulting mixture was kneaded together and extruded through a screen having a mesh of 0.7 mmφ to obtain granules, which were then dried at 50° C. for 5 hours and sieved to obtain a granule product containing 50 mg of MTB/500 mg of the product.

EXAMPLE 5

Ten grams of MTB and 20 g of hydroxypropyl methyl cellulose were added to and dissolved in 200 ml of a mixture of dichloroethane and ethanol (1/1). To the mixture obtained, there was added 20 g of light silicic acid anhydride, and the resulting mixture was uniformly mixed and dried by distilling off the solvent under a reduced pressure to obtain a powder. After being passed through a 40-mesh sieve, the powder was uniformly mixed with 50 g of mannitol to obtain a powder product.

EXAMPLE 6

To 100 g of MTB dissolved in 300 ml of a mixture of dichloroethane and ethanol (1/1), there was added 3 g of polysorbate-80. After the polysorbate was dissolved, 167 g of crystalline cellulose was added and uniformly mixed. Thereafter the resulting mixture was dried at 50° C. for 4 hours to obtain a powder, which was then uniformly mixed with 4 g of magnesium stearate. The mixed powder was charged into a No. 4 capsule in the amount of 137 mg of the powder per capsule to obtain a hard gelatin capsule product containing 50 mg of MTB per capsule.

EXAMPLE 7

A hundred grams of MTB was dissolved in 400 g of PEG having an average molecular weight of 400 to obtain a solution, which was mixed with 200 g of light silicic acid anhydride and 300 g of calcium carboxymethyl cellulose to obtain a powder. The powder was passed through a 42-mesh sieve to obtain a powder product containing 50 mg of MTB per 500 mg of the product.

EXAMPLE 8

To a mixture of 100 g of MTB, 80 g of crystalline cellulose, 20 g of corn starch and 16 g of hydroxypropyl cellulose with a low degree of substitution, there was added 16 g of PVP and 4 g of polyoxyethylene hardened castor oil which were dissolved in 120 ml of ethanol. The resulting mixture was kneaded uniformly, granulated, dried at 50° C. for 4 hours and sieved to obtain granules. Four grams of talc was added to the granules, and the mixture was uniformly mixed and charged into a No. 4 capsule in the amount of 120 mg per capsule to obtain a hard gelatin capsule product containing 50 mg of MTB per capsule.

EXAMPLE 9

A hundred grams of MTB and 80 g of PEG having an average molecular weight of 6000 were dissolved in 500 ml of a mixture of dichloromethane and ethanol (1/1) to obtain a solution, to which 20 g of light silicic acid anhydride was added, followed by mixing, drying at 50° C. for 4 hours and pulverizing. To the powder obtained, there was added 88 g of crystalline cellulose, 10 g of carboxymethyl cellulose and 2 g of magnesium stearate and the resulting mixture was tableted in a conventional manner to obtain a tablet product containing about 50 mg of MTB per table.

EXAMPLE 10

To a mixture of 100 g of MTB, 80 g of crystalline cellulose, 36 g of corn starch and 10 g of hydroxypropyl cellulose with a low degree of substitution, there was added 10 g of PVP and 2 g of polysorbate-80 which were dissolved in 120 ml of ethanol, followed by kneading uniformly. The kneaded mixture was extruded through a screen having a mesh of 0.7 mmϕ to form granules, which was then dried at 50° C. for 5 hours and sieved. After adding 2 g of magnesium stearate, the granules were tableted in a conventional manner to obtain a tablet product having a diameter of 7 mm and a weight of 120 mg.

EXAMPLE 11

To 2 g of MTB dissolved in 10 g of acetone, there was added 0.2 g of polysorbate-80, followed by agitating and mixing. To the resulting solution, there was added 511.8 g of kaoline, followed by uniform mixing and drying to obtain a dried powder. Separately, 440 g of glycerine was heated to 100° C. to remove water therefrom, whereafter 45 g of boric acid was added to the glycerine to dissolve it. To this glycerine solution, there was added the above-mentioned dried powder. After cooling 0.5 g of thymol dissolved in 0.5 g of peppermint oil was added and the whole mixture was mixed thoroughly to obtain a cataplasm product.

The present medicine is an anti-asthmatic agent which inhibits the realse of histamine and SRS-A very effectively and prevents airway stenosis (decrease in respiratory volume) during asthma paroxysm very effectively.

Hereunder is explained the effect of the present medicine referring to test examples.

TEST EXAMPLE 1

Inhibitory effect of MTB on the release of histamine and SRS-A from guinea pig lung slices Test Procedure Hartley male guinea pigs were passively sensitized by intravenously administering 0.5 ml per head of anti-BAS guinea pig blood serum.

Lungs obtained after bleeding and killing the guinea pigs after 2 days were cut into slices, which were treated with fixed concentrations of the test medicines. After the passage of 5 minutes, the amounts of histamine and SRS-A released by the action of an antigen were measured, and a release-inhibition rate (%) was calculated in comparison with the release amount of the control group in which no treatment with the test medicine was conducted.

$$\text{Release-inhibition rate (\%)} = \frac{R_O - R}{R_O} \times 100\ (\%)$$

R: Release amount of the control group

R: Release amount of the test medicine-treated group

The test medicines employed were the present medicine MTB and, as comparative medicines, disodium cromoglicate (hereinafter referred to as DSCG) and tranilast (hereinafter referred to as N-5'). The test was conducted in a concentration range of $10^{-8}$ to $10^{-4}$ g/ml. Histamine was measured by the fluorescence method in accordance with the method of May, C. D. et al described in the Journal of Allergy, Vol. 46, pages 12–20, 1970, and SRS-A was measured by the Magnus method described in the Japanese textbook "Yakubutsugaku Jikken" (Experiments in Pharmacology) authored by Keijiro Takagi and Kikaru Ozawa and published by Nanzando, Japan.

Test Results

The results are shown in Table 1. Each of the measured values given in the table is the average of three measurements.

TABLE 1

| Concentration of the medicine (g/ml) | Release-inhibition rate (%) | | | | | |
|---|---|---|---|---|---|---|
| | Histamine | | | SRS-A | | |
| | MTB | DSCG | N-5' | MTB | DSCG | N-5' |
| $10^{-4}$ | 37 | 2 | 16 | 64 | 13 | 54 |
| $10^{-5}$ | 30 | 0 | 5 | 66 | 9 | 11 |
| $10^{-6}$ | 14 | | | 49 | | |
| $10^{-7}$ | 6 | | | 28 | | |
| $10^{-8}$ | 8 | | | 2 | | |
| Control | 0 | 0 | 0 | 0 | 0 | 0 |

As is clear from the results of Table 1, the present medicine, MTB, shows remarkably high histamine and SRS-A release-inhibition rates compared with those of known DSCG and N-5'. MTB shows particularly high SRS-A release-inhibition rates of 49 to 66% in the concentration of $10^{-6}$ to $10^{-4}$ g/ml.

TEST EXAMPLE 2

Inhibitory effect of MTB on the release of histamine and SRS-A from rhesus monkey lung slices Test Procedure Rhesus monkey lungs were cut into slices, which were passively sensitized with human atopy blood serum.

Thereafter the test was conducted in the same manner as in Test Example 1 to compare the histamine and SRS-A release-inhibition effect of the present medicine MTB with that of the known medicine DSCG.

Test Results

The results are shown in Table 2. Each of the measured values given in the table is the average of three measurements.

TABLE 2

| Concentration of the medicine (g/ml) | Release-inhibition rate (%) | | | |
|---|---|---|---|---|
| | Histamine | | SRS-A | |
| | MTB | DSCG | MTB | DSCG |
| $10^{-4}$ | 27 | 0 | 16 | 2 |
| $10^{-5}$ | 2 | 0 | 17 | 0 |
| $10^{-6}$ | 12 | | 18 | |
| $10^{-7}$ | 0 | | 0 | |
| Control | 0 | 0 | 0 | 0 |

TEST EXAMPLE 3

Inhibitory effect of MTB on the release of histamine and SRS-A from human lung slices Test Procedure A macrographically normal portion was sampled from a human lung excised in a lung cancer operation and was passively sensitized with human atopy blood serum in a similar manner to the case of the rhesus monkey lung slices mentioned above. Thereafter the histamine and SRS-A release-inhibiting effect of the test medicines was measured in the same manner as in Test Example 1.

Test Results

The results are shown in Table 3. Each of the measured values given in the table is the average of three measurements.

TABLE 3

| Concentration of the medicine (g/ml) | Release-inhibition rate (%) | | | | | |
|---|---|---|---|---|---|---|
| | Histamine | | | SRS-A | | |
| | MTB | DSCG | N-5' | MTB | DSCG | N-5' |
| $10^{-4}$ | 27 | 18 | 31 | 47 | 39 | 37 |
| $10^{-5}$ | 23 | 13 | 16 | 47 | 41 | 32 |
| $10^{-6}$ | 23 | | | 43 | | |
| $10^{-7}$ | 8 | | | 31 | | |
| $10^{-8}$ | 0 | | | 2 | | |
| Control | 0 | 0 | | 0 | 0 | 0 |

TEST EXAMPLE 4

Effect of preventing experimental asthma

Test Procedure

Guinea pigs passively sensitized with an anti-DNP-AS blood serum of guinea pig were placed in an airtight box and caused to inhale 2.5 mg/ml of DNP-BSA over 15 seconds through a nebulizer under non-narcosis and non-confinement conditions, whereby experimental asthma was caused. The fluctuation of the guinea pig thorax was recorded with a recorder through a differential pressure transducer to measure unit tidal volumes with the passage of time, whereby the rate of decrease in tidal volume was obtained in comparison with a value measured before causing the asthma.

The test medicines were MTB and N-5', each of which was orally administered in an amount of 250 mg/kg at 60 minutes prior to causing the asthma.

Test Results

The results are shown in Table 4. Each of the measured values given in the table is the average of seven measurements.

TABLE 4

| Time (min.) | Tidal volume-decrease rate (%) | | |
|---|---|---|---|
| | Control | MTB | N-5' |
| 0 | 0 | 0 | 0 |
| 1 | 34 | 17 | 26 |
| 2 | 48 | 17 | 24 |
| 3 | 47 | 21 | 24 |
| 4 | 46 | 23 | 26 |
| 5 | 42 | 21 | 23 |
| 6 | 41 | 22 | 25 |
| 8 | 39 | 21 | 28 |
| 10 | 34 | 21 | 24 |
| 15 | 30 | 14 | 27 |
| 20 | 25 | 19 | 22 |
| 30 | 29 | 15 | 19 |

As is clear from the results of Table 4, the group to which the present medicine, MTB, was administrated shows a remarkably low rate of decrease in unit tidal volume compared with those of the control group to which no medicine was administered and of the group to which the comparative medicine N-5' was administered. Particularly, the present medicine shows an excellent effect of controlling rapid decrease in unit tidal volume immediately after causing the asthma.

The acute toxicity of MTB on warm-blooded animals is shown in Table 5.

TABLE 5

| Animal | | Acute toxicity LD 50 (mg/kg) | | | |
|---|---|---|---|---|---|
| | | Administration Route | | | |
| | | i.v. | i.p. | s.c. | p.o. |
| Mouse | male | 1130 | 1120 | >4000 | >4000 |
| | female | 1225 | 1160 | >4000 | >4000 |
| Rat | male | 1110 | 1430 | >4000 | >4000 |

TABLE 5-continued

| | Acute toxicity LD 50 (mg/kg) | | | |
| --- | --- | --- | --- | --- |
| | Administration Route | | | |
| Animal | i.v. | i.p. | s.c. | p.o. |
| Dog female | 1160 | 1430 | >4000 | >4000 |
| male | — | — | — | >4000 |
| female | — | — | — | >4000 |

Animals tested were as follows.
Mouse: ddy, weight 20–23 g, 20 mice per group
Rat: wistar, weight 110–130 g 10 rats per group
Dog: beagle, weight 8 kg, 3 dogs per group The following test examples are shown to explain that the present medicine pharmaceutically prepared by the new preparation method shows remarkably high dissolution rate and bioavailability (concentration in blood).

TEST EXAMPLE 5

Dissolution Test

Test Procedure

As an eluate was used 500 ml of an artificial gastric juice (Japanese Pharmacopoeia, the first liquid). The artificial gastric juice was maintained at 37±0.5° C., and a test medicine containing 50 mg of MTB was placed on the bottom of a container containing the gastric juice. A paddle was rotated at 100 rpm and sampling was conducted at intervals of a fixed number of minutes to measure the amount of MTB dissolved in the gastric juice by spectrophotometry.

Test Medicines

Sample A of the present invention . . . Hard gelatin capsule product of Example 6

Sample B of the present invention . . . Tablet product of Example 10

Comparative sample A . . . Hard gelatin capsule product obtained by a conventional method Comparative sample B . . . Tablet product obtained by a conventional method.

Test Results

As shown in Table 6, the medicines of the present invention show a high dissolution rate.

TABLE 6

| | Dissolution rate (%) | | | |
| --- | --- | --- | --- | --- |
| | Hard gelatin capsule | | Tablet | |
| Time (min) | Sample A of this invention | Comparative sample A | Sample B of this invention | Comparative sample B |
| 5 | 77.6 | 3.6 | 51.2 | 2.1 |
| 10 | 87.8 | 6.2 | 60.0 | 3.7 |
| 20 | 98.0 | 12.3 | 84.3 | 6.8 |
| 30 | 99.8 | 17.6 | 93.6 | 9.5 |
| 40 | 101.4 | 22.5 | 97.8 | 10.9 |
| 60 | 98.7 | 31.7 | 98.4 | 12.0 |

The comparative medicines used in the test mentioned above were prepared in the following manner.

COMPARATIVE SAMPLE A

Fifty grams of MTB crystalline powder was uniformly mixed with 68 g of lactose and 2 g of magnesium stearate to obtain a mixture. 120 mg of the mixture was charged in a capsule to obtain a hard gelatin capsule product containing 50 mg of MTB per capsule.

COMPARATIVE SAMPLE B

A mixture of 50 g of MTB crystalline powder, 40 g of lactose, 15 g of corn starch, 10 g of crystalline cellulose powder and 3 g of starch paste was kneaded with about 40 ml of water and extruded through a screen having a diameter of 7 mm to obtain granules. To the granules, dried and sieved, there was added 2 g of magnesium stearate and the resulting mixture per tablet.

TEST EXAMPLE 6

Measurement of MTB Concentration in Blood

A test medicine was orally administered to a group of five beagle male dogs weighing about 10kg each, which were abstinent from food for 24 hours. At given intervals, blood was drawn from the dogs, and the MTB concentration in blood was measured by liquid chromatography.

Test Medicines
Same as in Test Example 5
Test Results
The results are shown in Table 7.

TABLE 7

| | Concentration in blood (µg/ml) | | | |
| --- | --- | --- | --- | --- |
| | Hardened capsule | | Tablet | |
| Time (min) | Sample A of this invention | Comparative sample a | Sample B of this invention | Comparative sample B |
| 15 | 0.23 | 0.04 | 0.14 | ND |
| 30 | 0.36 | 0.08 | 0.28 | 0.03 |
| 45 | 0.44 | 0.12 | 0.39 | 0.05 |
| 60 | 0.57 | 0.14 | 0.56 | 0.07 |
| 90 | 0.62 | 0.30 | 0.64 | 0.13 |
| 120 | 0.47 | 0.18 | 0.56 | 0.09 |
| 180 | 0.23 | 0.08 | 0.31 | 0.04 |
| 240 | 0.16 | 0.05 | 0.22 | 0.03 |
| 360 | 0.09 | 0.03 | 0.10 | ND |

Remarks
(1): Each of the values given in the table is the average over five dogs
(2): ND means that MTB was not detected.

As is clear from the above test examples, an antiasthmatic medicine having an excellent SRS-A release-inhibiting action can be provided by the present invention.

What is claimed is:

1. A process for preparing a SRS-A release-inhibiting composition containing 5-(3-n-butyloxalylaminophenyl)tetrazole having a high bioavailability, said process comprising (a) mixing 5-(3-n-butyloxalylaminophenyl)tetrazole with at least one dispersant selected from the group consisting of polysorbate-80, polyvinyl pyrrolidone, polyoxyethylene hardened castor oil, polyethylene glycol, hydroxymethyl cellulose, hydroxypropyl cellulose and hydroxypropyl methyl cellulose in coexistence with a non-aqueous solvent which can be easily removed and (b) removing the non-aqueous solvent from the mixture, wherein said dispersant is used in the range of 0.01 to 10 parts by weight per one part by weight of 5-(3-n-butyloxalylaminophenyl)tetrazole.

2. The process of claim 1, wherein said dispersant is polysorbate-80.

3. The process of claim 1, wherein said non-aqueous solvent is selected from the group consisting of methanol, ethanol, isopropanol, acetone and dichloromethane.

4. A process for preparing a SRS-A release-inhibiting composition containing 5-(3-n-butyloxalylaminophenyl)tetrazole having a high bioavailability, which comprises dissolving 5-(3-n-butyloxalylaminophenyl)-tetrazole in liquid polyethylene glycol, wherein said polyethylene glycol is used in the range of 4 to 10 parts by weight per one part by weight of 5-(3-n-butyoxalylaminophenyl)tetrazole.

5. The product was prepared by the process of claim 1.

6. The product was prepared by the process of claim 4.

7. A SRS-A release-inhibiting pharmaceutical composition, which comprises 5-(3-n-butyloxalylaminophenyl)tetrazole as prepared by the process of claim 1 in an amount showing a SRS-A release-inhibiting effect and a pharmaceutically acceptable carrier.

8. The pharmaceutical composition as claimed in claim 7 comprising about 10 to about 500 mg of 5-(3-n-butyloxalylaminophenyl)tetrazole.

9. A SRS-A release-inhibiting pharmaceutical composition, which comprises 5-(3-n-butyloxalylaminophenyl)tetrazole as prepared by the process of claim 4 in an amount showing a SRS-A release-inhibiting effect and a pharmaceutically acceptable carrier.

10. The pharmaceutical composition as claimed in claim 9 comprising about 10 to about 500 mg of 5-(3-n-butyloxalylaminophenyl)tetrazole.

* * * * *